(12) United States Patent
O'Hare et al.

(10) Patent No.: US 6,342,229 B2
(45) Date of Patent: *Jan. 29, 2002

(54) HERPESVIRUS PARTICLES COMPRISING FUSION PROTEIN AND THEIR PREPARATION AND USE

(75) Inventors: Peter Francis Joseph O'Hare, Surrey; Gillian Daphne Elliott, Kent, both of (GB)

(73) Assignee: Phogen, Limited, Cambridge (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/366,286

(22) Filed: Aug. 2, 1999

(30) Foreign Application Priority Data

Jul. 31, 1998 (GB) .............................. 9816761

(51) Int. Cl.⁷ .................. A61K 39/245; C12P 21/04
(52) U.S. Cl. ................. 424/229.1; 424/230.1; 424/231.1; 435/5; 435/69.7; 435/69.3; 435/320.1; 435/235.1; 435/252.3; 435/325; 536/23.4; 536/23.5; 536/23.72
(58) Field of Search ................ 435/5, 69.7, 69.3, 435/320.1, 235.1, 252.3, 325; 424/229.1, 230.1, 231.1; 536/23.4, 23.5, 23.72

(56) References Cited

FOREIGN PATENT DOCUMENTS

| WO | WO 92/05263 | 4/1992 |
|----|-------------|--------|
| WO | WO 94/21807 | 9/1994 |
| WO | WO 96/26267 | 8/1996 |
| WO | WO 97/05265 | 2/1997 |
| WO | WO 98/32866 | 7/1998 |
| WO | WO 98/42742 | 10/1998 |

OTHER PUBLICATIONS

Chalfie et al., *Green Fluorescent Protein as a Marker for Gene Expression*, Science 263:802–805 (1994).

Elliott et al., *The Herpes Simplex Virus Type I Tegument Protein VP22 Is Encoded By Gene UL49*, Journal of General Virology 73:723–726 (1992).

Fang et al . Gene Therapy, 1998, vol. 5, pp. 1420–1424.*

Leslie et al . Virology, Jun. 1996, vol. 220 (1), pp. 60–68.*

Prasher DC . Trends Genet, 1995, vol. 11 (8), pp. 320–323.*

* cited by examiner

*Primary Examiner*—Ali R. Salimi
(74) *Attorney, Agent, or Firm*—Klarquist Sparkman, LLP

(57) ABSTRACT

Herpesviral particle preparations, e.g. a preparation of herpesviral particles isolated from the cell culture in which such particles were produced, can have at least part of the VP22 tegument protein present in the form of a recombinant mutant form of VP22, e.g. as a recombinant fusion polypeptide comprising a VP22-active sequence and a non-VP22 peptide or polypeptide sequence such as a fluorescent GFP sequence: corresponding DNA preparations are described. The use of virus particles containing fluorescent fusion protein to detect the progress of cell infection by virus and to screen for neutralising antibody or inhibitors of infection is also described. Vaccine uses of modified herpesvirus particles are described.

16 Claims, 2 Drawing Sheets

HERPESVIRUS PARTICLES COMPRISING FUSION PROTEIN AND THEIR PREPARATION AND USE

FIELD OF THE INVENTION

This invention relates to modified herpesviruses and to materials and methods for their preparation, and to their uses, including uses in assays, in diagnostics and in immunotherapy and immunoprophylaxis.

BACKGROUND

The transport properties of VP22 protein are described for example in PCT WO 97/05265 (O'Hare and Elliott). Also described in that document are fusion products of VP22, including a fusion protein of VP22 with green fluorescent protein.

The present invention aims to provide herpesviral preparations comprising modified VP22 proteins, and a number of uses of such preparations.

SUMMARY AND DESCRIPTION OF THE INVENTION

An aspect of the invention provides herpesviral particles, e.g. a preparation of herpesviral particles isolated from the cell culture in which such particles were produced, in which at least part of the VP22 tegument protein is present as a fusion polypeptide comprising a VP22-active sequence and a non-VP22 peptide or polypeptide sequence selected from (a) sequences providing a detectable gene product, e.g. as a fusion with a gene encoding green fluorescent protein (GFP), and (b) immunogenic sequences corresponding to antigens associated with human disease.

The invention further provides herpesviral particles, e.g. a preparation of herpesviral particles isolated from the cell culture in which such particles were produced, in which at least part of the VP22 tegument protein is present in the form of a recombinant mutant form of VP22, for example, in the form of a recombinant fusion polypeptide comprising a VP22-active sequence and a non-VP22 peptide or polypeptide sequence. Among the herpesviral particles that can be produced in accordance with this aspect of the invention are particles with or without viral genomes, for example infectious herpesvirus particles, killed herpesviral particles, light particles and amplicons, (all of which can be made by techniques readily adaptable from or in accordance with per-se-known technique for producing herpesviral particles from virus types that do not incorporate the features described herein).

Also provided by the invention are DNA preparations including for example viral genomic DNA preparations in which there is present a VP22 recombinant fusion gene encoding a recombinant VP22 fusion polypeptide as already mentioned. The fusion polypeptide can for example be one that is detectable by fluorescence, e.g. a fusion protein derived from VP2 and green fluorescent protein (GFP).

In certain examples, the whole of the VP22 component of the virion can be of such a recombinant protein. For example, in a modified herpesvirus according to an example of the invention, the native VP22-encoding gene can have been replaced by a hybrid gene encoding a fusion product of VP22 with GFP.

Alternatively the viral particles can comprise normal/native VP22 along with modified or heterologous VP22. Such an example of the invention can e.g. comprise a mutant HSV which is gH-, i.e. deletant in respect of the essential viral gene encoding gH glycoprotein, and which has had a gene encoding a fusion product of VP22 and GFP inserted, under control of a promoter such as CMV IE promoter, at the locus of the deleted essential gene.

The herpesviral particles can be infectious herpesvirus, or otherwise can be of killed herpesvirus, or otherwise inactivated herpesvirus, or can be of defective herpesviral particles (e.g. herpesviral amplicons).

An infectious herpesvirus with a modified VP22 comprised in its tegument can be an attenuated virus, e.g. a virus carrying an attenuating mutation in its genome. 'Attenuating mutation' in this context is understood to comprise (i) mutations that reduce the virulence of the virus without preventing its replication on normal host cells, e.g. a virus with a tk-mutation, as well as (ii) lethal mutations in the presence of which the virus can only be grown on host cells that complement the lethal mutation, e.g. a virus with a gH-mutation.

The herpesvirus can be a mutant in which the sole copy of the VP22 gene has been mutated to encode the modified VP22 protein. Alternatively it can be a mutant in which a modified or heterologous VP22 gene has been inserted, with or without deletion of the native VP22 gene.

Alternatively again, the herpesvirus can be of wild-type in respect of its VP22 gene and can be grown and produced by infection of a host cell that expresses a modified or heterologous VP22. Under these circumstances the herpesvirus can if desired have a wild-type genome either entirely or at least in respect of VP22, although its tegument carries modified VP22 protein.

The invention provides isolated preparations of such herpesviral particles, i.e. substantially separated from the cell culture and medium that produced them, including pharmaceutical forms of such herpesviral particles, e.g. suitable for injection into a subject to be treated therewith, or inoculation into a cell preparation to be treated therewith for later pharmaceutical use.

The virus particles can be based on herpes viruses of various species. For example they can be based on herpes simplex virus, HSV1 or HSV2, or on VZV, BHV, EHV or MDV, among others.

The modified viruses can be used in a variety of ways. For example, they can be used as vaccines or vaccine components to provoke immune responses against the peptide fused with the VP22. Suitable antigens for incorporation in thsi connection can for example be those listed in WO 96/26267 (Cantab Pharmaceuticals Research Ltd).

In the case of viruses where the fused VP22 polypeptide comprises a deteactable protein such as for example GFP protein, the modified viruses can be used wherever simple fluorescent identification or detection of virus particles is desired, for example to detect virus particle formation at low levels in infected cell preparations.

For example, the invention further provides a process of using herpesviral particles where the fusion polypeptide sequence comprises a sequence providing a detectable VP22 fusion protein, to detect the progress of herpesviral infection of cells; the process comprises (i) contacting said particles with said cells and (ii) detecting said fusion protein within said cells. This can be particularly convenient where the protein is a fluorescent fusion protein and the fluorescence of the fusion protein is detected within the cells, e.g. fluorescence of GFP-VP22 fusion protein. The process can be used to detect the progress of cell infection by virus and/or to screen for neutralising antibody or inhibitors of infection of cells by virus.

Thus, for example, in this aspect of the invention, a process for using infectious viral particles as described herein comprises for example a test method such as a screening method for detecting the neutralisation of herpesviral particles: the process can comprise (a) treating infectious viral particles with a possibly-neutralising condition that is to be the subject of the test, e.g. treating the virus to a possible neutralising agent under test, such as for example a serum sample possibly containing a neutralising antibody; wherein, in the virus particles so treated, a gene encoding VP22 is present as a fusion with a gene having a detectable gene product, e.g. as a fusion with a gene encoding GFP, (or wherein the genome has another gene inserted or modified therein so that such gene has a readily-detectable gene product not normally expressed by corresponding wild-type virus, e.g. GFP or a fusion protein including GFP); (b) using said treated virus particles to infect host cells, and examining said host cells for the production therein of said detectable gene product. Presence of neutralising conditions can be sensitively and easily detected e.g. simply by observing green fluorescence or its absence in the culture of infected cells in the case where the gene product is GFP or a fusion protein related thereto: the fluorescence observed is then inversely related to the extent of virus neutralisation by the possibly neutralising conditions under test, and complete neutralisation can often be seen easily by absence of development of fluorescence compared to the result with an appropriate parallel control process using infectious virus.

Correspondingly, the process can be simply modified to function as a screen for any condition that is possibly inhibitory of virus replication.

Especially in this aspect of the invention, any of a variety of detectable genes and gene products can be used instead of GFP if desired: for example betagalactosidase gene and gene product or luciferase gene and gene product, both known per-se. In the case of beta-galactosidase, the gene product can be visualised and/or quantitated in the infected host cells in per-se known manner by a suitable substrate reaction, and the luciferase gene product can also be detected or quantitated in the infected cells by a suitable per-se known photogenic substrate. The GFP example is especially advantageous because its fluorescence can be immediately and simply visualised and requires no extra processing steps such as.

Other peptides incorporated for this purpose can be for example antigenic polypeptides, such as antigens of herpesvirus or papillomavirus, or of bacterial antigens against which an immune response is desired. Such preparations can for example be formulated in any suitable way known per se for viral vaccines.

Embodiments of the invention are described below by way of example only but without intent to limit the invention, and reference is made to the accompanying drawings, in which.

Figure 1:
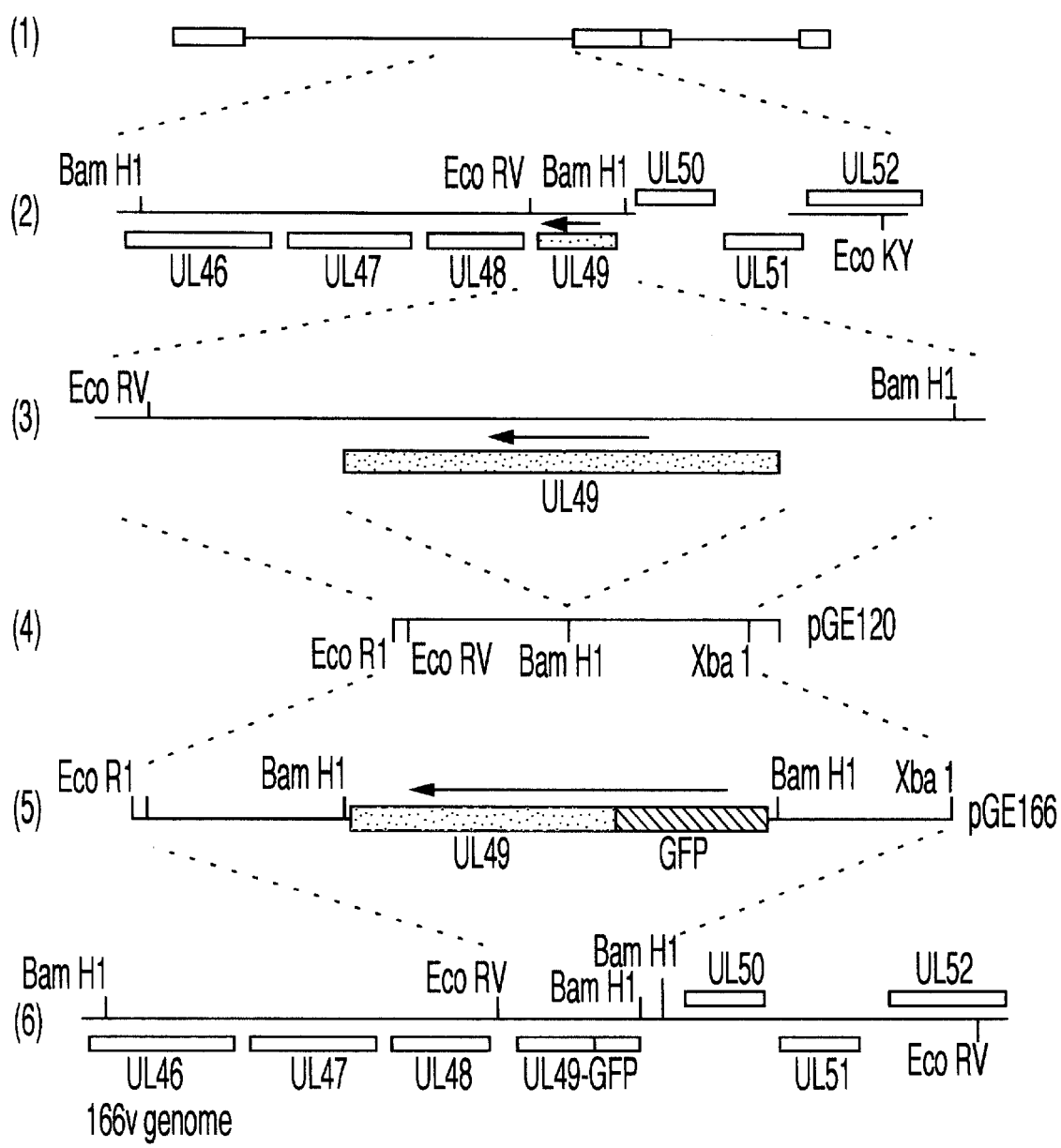
FIG. 1 shows diagrammatically stages in the construction of a virus encoding a VP22-GFP fusion protein in place of the native UL49/VP22 gene.

A general reference to the Aequoria jellyfish) green fluorescent protein GFP and its use is Chalfie M, Tu Y, Euskirchen G, Ward W, and Prasher D, (1994): "Green fluorescent protein as a marker for gene expression" Science 263, 802–805.

In certain examples below, the starting HSV virus strains are deletants in respect of the essential gH gene, and are cultured on cell lines expressing viral gH—see for example specifications WO 92/05263 and WP 94/21807, incorporated herein by reference. The gH deletant viruses are referred to below as DISC viruses. Corresponding and other examples of the invention can also be made on the basis of parental viruses that are not gH-deletant, e.g. from wild-type HSV strains, e.g. as described further below.

Construction of HSV Viruses (deleted in respect of gH) Expressing Gene Fusions of VP22 and Green Fluorescent Protein Preparation of Plasmid Constructs In order to insert gene(s) of interest into a DISC HSV virus, plasmids were constructed in which a CMV promoter, the gene of interest and a polyadenylation sequence (together termed the expression cassette) were ligated between (PacI) restriction sequences. HSV1 and HSV2 viruses used as parental strains for this construction had had the gH gene deleted (see for example WO 92/05263 and WP 94/21807), and had further been mutated by site-directed mutagenesis to insert a PacI restriction site at the site of the deleted gH gene. This allowed the excision of the expression cassette from the plasmid by digestion with PacI and the subsequent ligation into PacI-digested virus DNA.

Three plasmids were constructed, containing expression cassettes containing VP22-gfp, gfp-VP22 and gfp coding sequences.

Construction of a Plasmid Construct to Express VP22-egfp from a DISC Virus

Plasmid pIMJ2 was digested with XbaI, phosphatased with CIP and purified by phenol-chloroform extraction and ethanol precipitation. Plasmid pGE150 was digested with XbaI and NheI and the resulting fragment purified from an agarose gel using Promega 'Wizard' purification kit. The purified fragment was ligated into XbaI-digested pIMJ2 and the ligation used to transform E. coli DH5 alpha. Resultant colonies were screened and the correct plasmid, termed pVP1, prepared.

To remove additional sequence between the promoter and the initiation codon of VP22-gfp, plasmid pVP1 was digested with HindIII, the vector purified from the intervening fragment and religated. The resultant plasmid, termed pVP2, was prepared.

Construction of a Plasmid Construct to Express egfp-VP22 from a DISC Virus

Plasmid pIMJ2 was digested with XbaI, phosphatased with CIP and purified by phenol-chloroform extraction and ethanol precipitation. Plasmid pGE155 was digested with XbaI and NheI and the resulting fragment purified from an agarose gel using Promega Wizard purification kit. The purified fragment was ligated into XbaI-digested pIMJ2 and the ligation used to transform E. coli DH5 alpha. Resultant colonies were screened and the correct plasmid, termed pVP3, prepared.

To remove additional sequence between the promoter and the initiation codon of VP22-gfp, plasmid pVP3 was digested with NotI and AgeI, treated with Klenow to remove overhanging DNA ends and religated. The ligation mix was used to transform E. coli DH5 alpha and plasmid prepared from resultant colonies. The DNA sequence between the promoter and the initiation codon was obtained and one clone, termed pVP4 a, was selected for preparation of the recombinant DISC virus. In this clone, an additional 51 bp to the 5' of the NotI site had been removed thereby optimising the distance between the promoter and the initiation codon.

Construction of a Plasmid Construct to Express egfp from a DISC Virus

Plasmid pIMJ2 was digested with HindIII and NheI and the cut vector purified from an agarose gel using Promega Wizard PCR prep kit. Plasmid EGFP-N1 (Clontech) was digested with HindIII and Not I and the subsequent fragment purified from an agarose gel. The fragment was then ligated into HinDiii/NotI-digested pIMJ2 and the ligation mix used to transform *E. coli* DH5 alpha. Resultant colonies were screened and the correct clone, termed pVP5, prepared.

Construction of Recombinant DISC Viruses

The strategy outlined below was used to make three recombinant DISC viruses.

Preparation of Insert 20 micro-g of each plasmid (pVP2, pVP4 a and pVP5) was digested with PacI and the resultant fragment purified from an agarose gel using Promega Wizard PCR purification kit. The amount of DNA in the resulting preparation was estimated by measuring the absorbance at 260 nm.

The DNA fragment was ligated into PacI-digested dH2 G virus DNA in a 50 micro-1 ligation reaction containing 1 micro-g virus DNA. Different ratios of virus DNA to fragment were tried but it was subsequently found that ligations containing beween 0.02–0.2 micro-g fragment were most successful.

Following overnight ligation at 15 deg C., ligation mixes were used to transfect CR2 cells using lipofectamine. After incubating at 37 deg C. for 72–90 h, cells were removed from the dish and sonicated to release virus. Serial dilutions of the sonicated cell/virus preparation were then applied to CR2 cells and overlaid with agarose. After 72 h at 37 deg C., resultant plaques were viewed by inverted fluorescence microscopy and plaques exhibiting green fluorescence marked. Marked plaques were picked using a Pasteur pipette to suck up the agarose and the resultant agarose plug used to inoculate CR2 cells. This enrichment procedure was repeated a further 2 times such that on viewing virus plaques by inverted fluorescence microscopy, no non-fluorescing plaques could be seen.

Master and working virus stocks were then prepared from the plaque-purified virus preparation and the titres measured by TC-ID50 calculation.

The resuling viruses were designated:

pVP2.1a(iv) DISC type 2 expressing VP22-egfp fusion protein;

pVP4a.3 b(i) DISC type 2 expressing egfp-VP22 fusion protein;

pVP5.2f(ii) DISC type 2 expressing egfp protein.

Abbreviations:

gfp: green fluorescent protein

VP22-gfp: a gene fusion of VP22 and gfp with the gfp coding sequence fused to the 3' end of the VP22 coding sequence gfp-VP22: a gene fusion of VP22 and gfp with the gfp coding sequence fused to the 5' end of the VP22 coding sequence BGH poly A: Polyadenylation sequence from bovine growth hormone gene CIP: Calf Intestinal Phosphatase Materials:

Plasmids/DNA:

pIMJ2: A plasmid derived from pRc/CMV (Invitrogen) containing a CMV promoter, multiple cloning site and BGH polyadenylation sequence between 2 PacI sites.

pGE150: A plasmid, derived from pEGFPN1 (Clontech) containing VP22-egfp gene fusion under the control of a CMV promoter.

pGE155: A plasmid, derived from pEGFPC1 (Clontech) containing egfp-VP22 gene fusion under the control of a CMV promoter.

dH2 G: DNA purified from DISC type 2 virus dH2 G (deletant in respect of gH and modified to include a PacI restriction site at the site of the deleted gH gene) and digested with restriction enzyme, PacI Restriction Enzymes: XbaI, NheI, HindIII, NotI, PacI, AgeI DNA modifying enzymes: Calf Intestinal Phosphatase (CIP); T4 ligase; DNA polymerase I large (Klenow) fragment DNA purification kits: Promega 'Wizard' mini prep kit (small scale plasmid preparation); Qiagen Maxi prep kit (large scale plasmid preparation); Promega 'Wizard' PCR prep kit (purification of DNA fragments)

Reagents: Phenol, chloroform, iso-amylalcohol 25:24:1 (v:v:v:) 200 mM EGTA Ethanol:

*E.coli* strains: *E. coli* DH5 alpha.

Alternative Embodiments of the Invention

Materials suitable for carrying out alternative embodiments of the invention are for example as follows:

Alternative source of GFP: Plasmid pEGFP-N1 containing an enhanced version of GFP is commercially available from Clontech. A 3755 bp DNA fragment can be generated from joint digestion of pEGFP-N1 using AseI and BsaI, and contains CMV promoter-GFP-polyA as well as the neomycin cassette. This can for example be cloned by blunt-end ligation in known manner into a desired contruct with suitable or suitably modified terminal sequences.

C-terminal Fusion of VP22 to GFP:

VP22 can be fused at its C-terminus to the coding sequence of the 27 kD green fluorescent protein (GFP) (Chalfie et al, 1994), to produce a fusion protein of around 65 kD.

A GFP expression vector, pEGFPN1 is obtainable from Cambridge Biosciences. A plasmid pGE150 can be constructed by inserting the BamH1 fragment from pUL49 ep, containing the entire VP22 open reading frame, into the BamH1 site of pEGFPN1, resulting in a fusion between VP22 and GFP.

COS-1 cells in 6 mm dishes can be transfected with a plasmid encoding VP22 GFP, site of the plasmid pGFP-N1 (Clontech), resulting in a fusion of VP22 to the N-terminus of green fluorescent protein (GFP). 40 hrs after transfection the cells can be harvested and high salt extracts prepared. Western blotting of these extracts demonstrates VP22 present in the extracts.

The plasmid encoding VP22-GFP can be inserted into a HSV virus genome in any suitable desired manner.

Further embodiments of the invention can be made, e.g. based on wild-type herpesvirus HSV1, in which the native VP22 gene is replaced using per-se known procedural steps for the homologous recombination, with a fusion gene, e.g. based on WO 97/05265 (O'Hare and Elliott), comprising a coding sequence for GFP either upstream or downstream of the coding sequence for VP22, still under the control of the native VP22 promoter. The resulting virus can be cultured on Vero cells using ordinary technique for HSV, and in the resulting virus particles all of the VP22 component is represented by a fusion protein with GFP. An example of such a virus is as follows:

Construction of an HSV-1 Recombinant Virus Expressing GFP-22

Construction of a HSV1 Recombinant Virus Expressing GFP-22, according to an example of the invention, is shown diagrammatically in FIG. 1.

The HSV-1 structural protein VP22 is encoded by the UL49 gene (GD Elliott et al, 1992, J gen Virol 73, pp 723–6) located in the Bam F restriction fragment of the long unique region of the genome (FIG. 1, lines 1 and 2). ULA9 was replaced with the gene encoding GFP-22 as follows:

The 400 bp flanking sequences of the HSV- 1 UL49 gene (FIG. 1, line 3) were amplified together by PCR from purified genomic DNA, to construct a single 800 bp fragment incorporating an EcoR1 site at one end and an Xba1 site at the other, together with a BamH1 site engineered in place of the UL49 gene (FIG. 1, line 4). This was inserted into plasmid pSP72 (Promega) as an EcoR1/Xba1 fragment to produce plasmid pGE120 (FIG. 1, line 4). A GFP-UL49 cassette contained on a BamH1 fragment was then inserted into the BamH1 site of pGE120 to produce plasmid pGE166 (FIG. 1, line 5), which contained a GFP-UL49 open reading frame surrounded by the UL49 flanking sequences, and hence driven by the UIA9 promoter.

Equal amounts (2 micro) of plasmid pGE166 and purified infectious HSV-1 strain 17 DNA were transfected into $1 \times 10^6$ COS-1 cells grown in a 60 mm dish using the calcium phosphate precipitation technique modified with BES (N,N bis (2 hydroxyethyl) 2 aminoethanesulphonic acid) buffered saline in place of HEPES-buffered saline, and incubated for four days, until cytopathic effect was present in all cells. After four days, virus was harvested from the infected cells into the cell medium, subjected to x3 freeze-thawing and resulting virus titrated on Vero cells. Around 6000 plaques were then plated on to Vero cells and screened for recombinants by GFP fluorescence.

Green plaques were detected and further plaque purified (twice). A selected example of a virus plaque showing the wanted fluorescence was designated 166v (FIG. 1, line 6).

Figure 2:
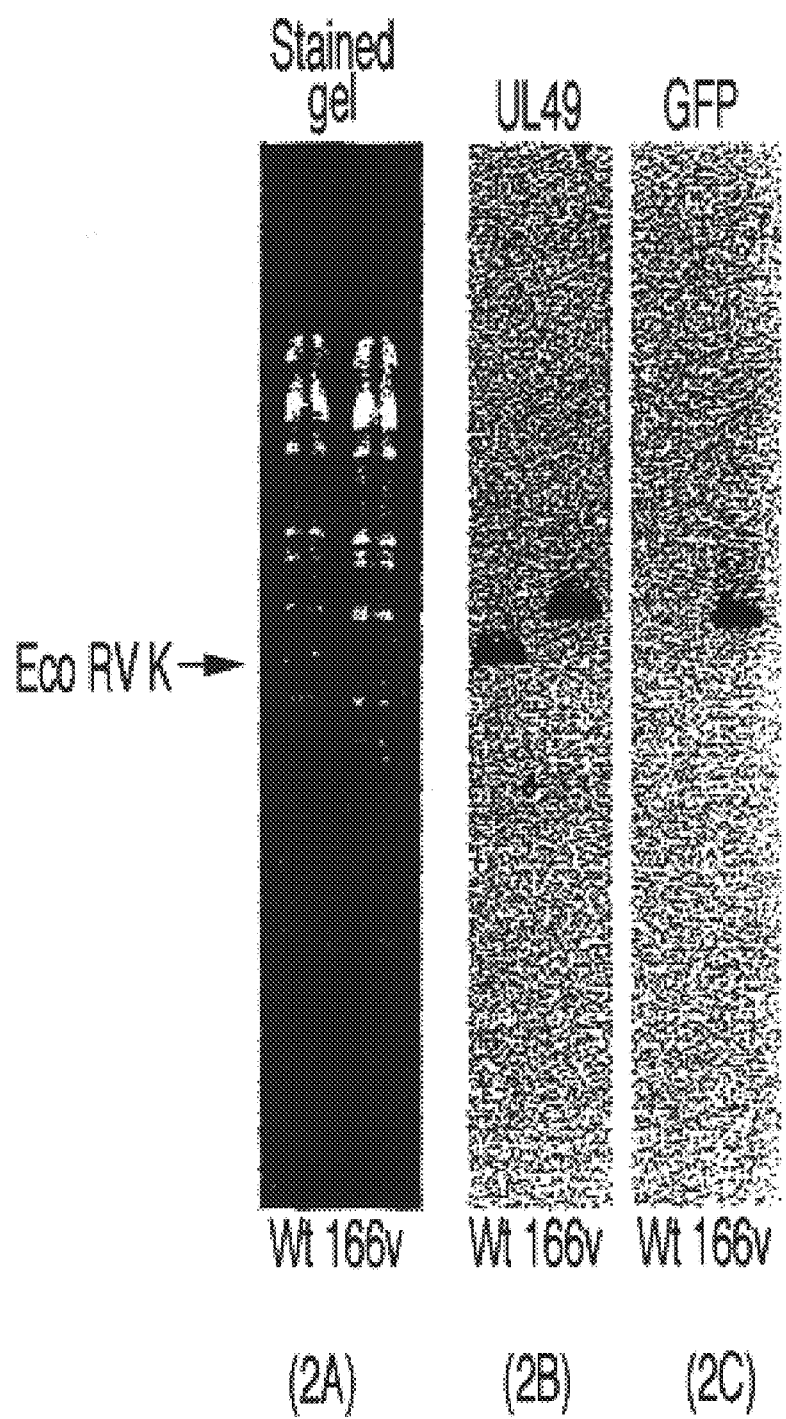
FIG. 2 shows agarose gels derived from restriction digests of a virus resulting from the construction described in connection with FIG. 1, for the purpose of verifying the constitution of the virus so constructed.

To verify that recombination had taken place in the correct location on the genome, and that the endogenous copy of the VP22 gene had been replaced by the GFP-22 gene, genomic DNA was purified from both parental/wild-type (strain 17) virus and the selected 166v virus, and subjected to restriction digestion with EcoRV (FIG. 2). Incorporation of GFP-22 into the genome should result in an increase in size of the EcoRV K fragment of the genome from 5.55 kb to 6.3 kb (FIG. 1, compare line 2 with line 6). The restriction pattern of of EcoRV digested virus DNA shows the loss of the original 5.55 kb fragment in the recombninant virus and the appearance of a larger fragment of 6.3 kb (FIG. 2A, stained gel). Southern blotting carried out on this gel using both a UL49 probe and a GFP probe (FIGS. 2B and 2C, UL49 and GFP) indicated that this new larger fragment hybridized to both sequences, and only the larger fragment hybridized to the GFP probe (FIG. 2C), confirming the presence of the GFP-22 fusion gene in the EcoRV K fragment.

When HSV1 virus particles of the GFP-VP22 (166V) and parental type, obtained from infected cell media and purified on 5–15% ficoll gradients, and subjected to SDS-PAGE analysis and Coomassie blue staining or Western blotting, results showed that the virion proteins corresponded with what would be expected as a result of the genome changes: i.e. the 166v virus contained a 65 kD protein species, as expected for a GFP-22 fusion protein, in place of the normal 38 kD VP22 species, and results obtained by the use of anti-VP22 and anti-GFP antibodies confirmed that the new virion component represented the expected fusion protein.

Fluorescence of the 166 v virus can be detected by fluorecence microscopy on the outer surface of for example Vero cells e.g. in a layer exposed to contact with the virus, e.g. at MOI 10.

The virus expressing a fluorescent structural protein can be localised by fluorescence via the fluorescent protein within a cell at various stages of infection of the cell by the virus.

Thus a herpes virus incorporating an indicator, e.g. a fluorescent indicator, as part of a structural protein of the virus, as described herein, can be used as a tool for study of the process of infection of cells by herpes virus. This should be of considerable use to researchers wishing to study and analyse the processes of virus infection.

The indicator effect provided by use of the present invention can be combined with the effects described in prior patent applications WO 97/05265 and WO 98/32866 (Marie Curie: P O'Hare & G D Elliott) both of which are hereby incorporated by reference in their entirety.

It has also been found that the 166 v virus infection increases the stability of cellular microtubules as efficiently as infection with the wild-type virus, thus a virus expressing VP22-GFP according to an example of the invention, and the corresponding VP22-GFP protein, can be used in place of other VP22 proteins to bring the indicator effect described herein in connection with all the purposes described in WO 98/42742 (Phogen Ltd: G D Elliott), also hereby incorporated by reference in its entirety.

The invention is susceptible of modifications and variations as will be apparent to readers skilled in the art. The present disclosure extends to combinations and subcombinations of the several features mentioned or described herein and in the references. The cited documents are hereby incorporated by reference in their entirety for all purposes.

What is claimed is:

1. A composition comprising herpesviral particles, in which a VP22 component of said herpesviral particles comprises a recombinant fusion polypeptide comprising a VP22 sequence and a non-VP22 peptide or polypeptide sequence wherein said fusion polypeptide is formed as a detectable fluorescent gene product, and wherein said viral particles are herpesviral particles in which a viral gene essential for production of infectious new virus has been deleted.

2. A composition according to claim 1, wherein the fusion polypeptide is a VP22-green fluorescent protein (VP22-GFP) fusion polypeptide.

3. A composition according to claim 1, wherein the entire VP22 component of the virion is said fuision polypeptide.

4. A composition according to claim 1, wherein the essential viral gene is the gH gene.

5. A composition according to claim 1, wherein said herpesviral particles are selected from: infectious herpesvirus, and killed or inactivated herpesvirus, and defective herpesvirus amplicons.

6. A composition comprising herpesviral particles for use in vitro, in which a VP22 component of said herpesviral particles comprises a recombinant fusion polypeptide comprising a VP22 sequence and a non-VP22 peptide or polypeptide sequence wherein said fusion polypeptide is formed as a detectable fluorescent gene product.

7. A composition according to claim 6, wherein the fusion polypeptide is a VP22-green fluorescent protein (VP22-GFP) fusion polypeptide.

8. A composition according to claim 6, wherein the entire VP22 component of the virion is said fusion polypeptide.

9. A method of detecting the progress of herpesviral infection of a preparation of cells, which method comprises (i) contacting a composition comprising infectious herpesviral particles, in which a VP22 component of the herpesviral particles comprises a recombinant fusion polypeptide comprising a VP22 sequence and a non-VP22 peptide or polypeptide sequence such that said fusion polypeptide is formed as a detectable gene product, with cells in vitro in which herpesviral infection is desired to be detected, and (ii) detecting infection caused by said herpesviral particles by detecting presence of said fusion polypeptide within said cells.

10. A method according to claim 9, wherein the fusion polypeptide is a fluorescent fusion polypeptide and said detection comprises detecting the fluorescence of said fusion polypeptide within said cells.

11. A method according to claim 10, wherein said fusion polypeptide is a VP22-green fluorescent protein (VP22-GFP) polypeptide.

12. A method of screening for agents which can neutralize infectivity of herpesviral particles, which method comprises (i) contacting a composition that comprises infectious herpesviral particles, in which a VP22 component of the herpesviral particles comprises a recombinant fusion polypeptide comprising a VP22 sequence and a non-VP22 peptide or polypeptide sequence providing a detectable gene product, with a neutralizing agent under test, to form treated herpesviral particles, and then (ii) infecting cells in vitro with the treated herpesviral particles, and then (iii) detecting any infection caused by said composition by detecting presence of said fusion polypeptide within said cells.

13. A method according to claim 12, wherein said fusion polypeptide is a fluorescent fusion polypeptide and said detection step comprises detecting fluorescence of said fusion polypeptide within said cells.

14. A method according to claim 13, wherein said fusion polypeptide is a VP22-green fluorescent protein (VP22-GFP) polypeptide.

15. A method of detecting the progress of herpesviral infection of cells, which method comprises, (i) contacting a composition comprising infectious herpesviral particles, wherein said viral particles are herpesviral particles in which a viral gene essential for production of infectious new virus has been deleted, and in which a VP22 component of the herpesviral particles comprises a recombinant fusion polypeptide comprising a VP22 sequence and a non-VP22 peptide or polypeptide sequence such that said fusion polypeptide is formed as a detectable gene product, with cells in vivo, in which herpesviral infection is desired to be detected, and (ii) detecting infection caused by said herpesviral particles by detecting presence of said fusion polypeptide within said cells.

16. A method according to claim 15, wherein the fusion polypeptide is a fluorescent fusion polypeptide and said detection comprises detecting the fluorescence of said fusion polypeptide within said cells.

* * * * *

UNITED STATES PATENT AND TRADEMARK OFFICE
CERTIFICATE OF CORRECTION

PATENT NO. : 6,342,229 B2
DATED : January 29, 2002
INVENTOR(S) : O'Hare et al.

It is certified that error appears in the above-identified patent and that said Letters Patent is hereby corrected as shown below:

Column 1,
Line 57, "VP2" should be -- VP22 --.

Column 3,
Line 63, "jellyfish)" should be -- (jellyfish) --.

Column 4,
Lines 29-30, a blank line should be inserted before the heading "Construction of a Plasmid Construct to Express VP22-egfp from a DISC Virus".
Lines 45-46, a blank line should be inserted before the heading "Construction of a Plasmid Construct to Express egfp-VP22 from a DISC Virus".

Column 5,
Lines 1-2, a blank line should be inserted before the heading "Construction of a Plasmid Construct to Express egfp from a DISC Virus".
Line 10, a blank line should be inserted before the heading "Construction of Recombinant DISC Viruses".
Line 13, a blank line should be inserted before the heading "Preparation of Insert".

Column 6,
Line 47, after "GFP," and before "site" the following should be inserted -- constructed by insertion of the UL49 open frame reading frame into the BamH1 --.

Column 7,
Line 9, "ULA9" should be -- UL49 --.
Line 11, "HSV- 1" should be -- HSV-1 --.
Line 23, "UIA9" should be -- UL49 --.

UNITED STATES PATENT AND TRADEMARK OFFICE
CERTIFICATE OF CORRECTION

PATENT NO. : 6,342,229 B2
DATED : January 29, 2002
INVENTOR(S) : O'Hare et al.

It is certified that error appears in the above-identified patent and that said Letters Patent is hereby corrected as shown below:

Column 8,
Lines 1 and 19, "166 v" should be -- 166v --.

Column 9,
Line 14, "polypeptidc" should be -- polypeptide --.

Signed and Sealed this

Twenty-ninth Day of July, 2003

JAMES E. ROGAN
*Director of the United States Patent and Trademark Office*